United States Patent [19]

Theis et al.

[11] Patent Number: 4,541,960

[45] Date of Patent: Sep. 17, 1985

[54] METHOD FOR PREPARING CYANACETALDEHYDE ACETALS

[75] Inventors: Christoph Theis, Bornheim; Gudrun Fickert, Troisdorf, both of Fed. Rep. of Germany

[73] Assignee: Dynamit Nobel Aktiengesellschaft, Cologne, Fed. Rep. of Germany

[21] Appl. No.: 500,471

[22] Filed: Jun. 2, 1983

[30] Foreign Application Priority Data

Jun. 16, 1982 [DE] Fed. Rep. of Germany ....... 3222519

[51] Int. Cl.[4] ................. C07C 120/00; C07C 121/16; C07C 121/46; C07C 121/75
[52] U.S. Cl. .............................. 260/464; 260/465 F; 260/465.6
[58] Field of Search ................. 260/465.6, 465 F, 464; 568/592, 594

[56] References Cited

U.S. PATENT DOCUMENTS 3,466,317  9/1969  Kuper ................................ 260/465.6
4,299,777  11/1981  Garrou et al. ................... 260/465.6

OTHER PUBLICATIONS

McElvain et al., J.A.C.S., 69 (1947), pp. 2657–2660.
Patai (Editor), "The Chemistry of the Ether Linkage", (1967), pp. 322–323, Interscience Pub., N.Y.

*Primary Examiner*—Joseph Paul Brust
*Attorney, Agent, or Firm*—Felfe & Lynch

[57] ABSTRACT

Cyanacetaldehyde acetals, which can be substituted at the alpha carbon atom, form in a high yield and purity by the transposition of the appropriately substituted 3-alkoxy-nitriles with alcohols in the presence of basic catalysts from the group of the alcoholates of the alkali or alkaline earth metals, followed by deactivation of the catalyst. Short reaction times and high yields combined with a minimum production of byproducts are achieved by the continuous performance of the transposition in the continuous-flow reactor.

17 Claims, No Drawings

METHOD FOR PREPARING CYANACETALDEHYDE ACETALS

BACKGROUND OF THE INVENTION

The invention relates to a continuous method for the preparation of substituted or unsubstituted cyanacetaldehyde acetals by the reaction of alpha-carbon-substituted or unsubstituted beta-alkoxy-acrylonitriles with alcohols in the presence of catalytic amounts of a suitable base at elevated temperature.

According to Am. Chem. Soc. 69 (1974) pages 2657–2660, the treatment of beta-ethoxyacrylonitrile with alcohol in the presence of small amounts of sodium ethoxide leads to the formation of the cyanoacetal by the quantitative addition of the alcohol. Separation of the product, however, is difficult, because the attempt to isolate it by heating with a few drops of concentrated sulfuric acid led to the reformation of the beta-ethoxyacrylonitrile starting substance in the amount of only 40%. According to the inventor's own studies, the reaction is incomplete and the transposition, even on the hundred-gram scale of operation, requires a great amount of time, and in the case of larger quantities the purity of the products is decidedly reduced.

Other methods of preparation, for example by the transposition of bromoacetaldehyde acetal with alkali cyanides or of beta-chloracrylonitrile with sodium alcoholate and alcohols are difficult to practice, the starting substances are difficult to obtain, and the yields achieved are moderate.

These known methods of preparation also can be practiced only discontinuously, the processing of the reaction solutions, such as neutralizations and separation of solids, is difficult and time-consuming, and calls for a great amount of safety measures and environmental safeguards.

The aim to be accomplished was therefore to prepare cyanacetaldehyde acetals by an economical and easily accomplished method, preferably adapted to a continuous industrial procedure. It is also desired to have the reaction go virtually to completion in a reasonably short period of time, to allow production of the product in pure form.

THE INVENTION

The invention is a method of preparing cyanacetaldehyde acetals of the formula

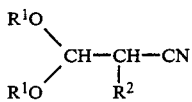
    I wherein $R^1$ represents identical or different straight-chain or branched alkyl moieties of 1 to 20 carbon atoms, or $-(CH_2)_m-Cyc$, Cyc being isocyclic or heterocyclic, mononuclear or polynuclear, aromatic or cycloaliphatic ring systems bearing, in some cases, substituents on the rings, with $m=0$ to 5, or one of the moieties $R^1$ or both of the moieties $R^1$ representing $-(CH_2)_p-OH$ or $-(alkylene)_p-OH$ with $p=2$ to 6, which are interrupted in some cases by one or more hetero atoms, or the two moieties $R^1$ together form an alkylene or alkenylene moiety of 2 to 6 carbon atoms which is interrupted in some cases by one or more hetero atoms, and wherein $R^2$ represents H, $R^1$, straight-chain or branched moieties $-(CH_2)_m-OR^3$ or $-(CH_2)_m-CH(OR^3)_2$, $R^3$ representing alkyl moieties of 1 to 12 carbon atoms and m and Cyc having the meanings given above, characterized in that compounds of the formula

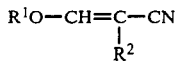
    II wherein $R^1$ and $R^2$ have the above meaning, are reacted with alcohols of the formula

    III wherein $R^1$ has the same meaning, in the presence of a basic catalyst of the formula

    IV wherein M is an alkali metal with $n=1$ or an alkaline earth metal with $n=2$ and $R^1$ has the same meaning as above, and which is dissolved or suspended in the alcohol component, at elevated temperature, and the catalyst is deactivated after the reaction has taken place.

The substituents $R^1$ and $R^2$ are generally those which are inert in the reaction. The starting substances II bear preferably alkyl moieties, of which those of 1 to 3 carbon atoms, especially the ethyl and the methyl moieties, are greatly preferred.

The moiety $R^2$ very preferably represents hydrogen, and methyl, ethyl, phenyl or benzyl are also preferred. If the moiety Cyc is present, isocyclic or heterocyclic ring systems of 5 or 6 ring members are preferred; the isocyclic rings—i.e., those containing only carbon as ring member—are especially those of benzene and cyclopentane to cycloheptane, and the heterocyclic rings—i.e., those containing ring-forming atoms in addition to carbon atoms may contain oxygen, nitrogen, sulfur, phosphorus or other atoms as heteroatoms, and especially mononuclear rings containing 1 or 2 atoms of oxygen, nitrogen, or sulfur.

The moiety $R^1$ is preferably an alkyl moiety of 1 to 3 carbon atoms, especially ethyl or methyl or the moiety of a diol, especially that of ethylene glycol to butylene glycol, any interrupting hetero atoms being as stated above. The moiety $R^1$ in the basic catalyst is to be the same as the moiety $R^1$ of the alcohol, with exceptions.

The moiety $R^3$ is preferably ethyl or methyl.

If one or both of the moieties $R^1$ are those of a saturated or unsaturated diol, the reaction is preferably carried out to such an extent that this moiety $R^1$ is preserved and, if desired, the cyclic acetal containing an alkylene or alkenylene moiety is formed in a second step.

In this method, the basic catalyst is preferably placed in the reaction vessel after dissolution in alcohol.

Preferably also, the nitrile component II and the alcohol component II containing the catalyst IV are fed simultaneously to the reactor via separate routes.

Thirdly, the reaction components are preferably thoroughly mixed and brought to reaction as quickly as possible by heating.

Sodium is greatly preferred as the metal M in the alcoholate, and potassium and calcium are also preferred.

Very preferably, the reaction components are thoroughly mixed directly at the point of entry, and then this reaction mixture flows through a reaction zone held at the reaction temperature by a thermostat, remaining therein for a specific average time, and it is then cooled.

The average time of stay in the reaction zone is the quotient of the fill capacity of the reactor and the sum of the volumes of the starting substances at 20° C. which are fed into the reactor per hour.

By a continuous process of this kind, preferably in a continuous-flow reactor, the desired transformations and yields are achieved and secondary reactions are very largely suppressed.

The reaction components can be metered into the reactor at ambient temperature, but to achieve short times of stay the components are to be preheated to approximately the reaction temperature and then they are to be metered into the reactor.

It is of critical importance to the performance of the continuous process and to its advantages to meter the basic catalysts continuously into the reaction zone, which can be done most simply by the preferred method of dissolving the catalyst in the alcohol that is used.

The catalyst can be deactivated after the reaction by neutralization with glacial acetic acid, which is common practice for the decomposition of alcoholates. This results, however, in disadvantages in the nonaqueous medium due to falsification of the pH measurement and especially to the formation of a highly viscous suspension from the reaction solution, which is very difficult to handle. Therefore it is greatly preferred in accordance with the invention to deactivate the catalyst with carbon dioxide or, in some cases, with an organic or inorganic acid. In addition to the preferred carbon dioxide, strong or medium-strong acids can be used, such as sulfuric acid, HCl gas, phosphoric acid or, for example, formic acid.

After the reaction mixture has cooled to room temperature, the deactivation can be performed batch-wise or continuously, in the case of carbon dioxide, by flooding with carbon dioxide or by feeding in carbon dioxide under pressure with good agitation. The separation of the sodium salts of the carboxylic acid half-esters corresponding to the alcohols that are used can be performed under a carbon dioxide atmosphere by filtration or centrifugation, but it is performed preferably by fractional distillation at reduced pressure, in the range from 0.1 to 500 mbar, for example, using, if desired, a fractionation column, together with the distillative processing of the reaction mixture. In this case the flooding of the reaction suspension or of the reaction solutions freed of the solid, as the case may be, with carbon dioxide during the distillative processing of the reaction mixture is of decisive importance to purity and yield. Fresh catalyst is added to the alcohol that has not been consumed in the reaction and has been removed by distillation, and the mixture is recycled. High-purity products are obtained if, in view of the thermal instability of the cyanacetaldehyde acetals, a distillation is performed at reduced pressure in the range from 0.1 to 50 mbar. A preliminary fraction, thus obtained, of the actual product fraction, contains the beta-alkoxyacrylonitrile that may not have reacted in the alcohol addition, as well as the beta-alkoxynitrile that re-forms as a result of thermal cleavage, along with large percentages of product. These preliminary fractions, mixed with beta-alkoxyacrylonitrile if desired, can be recycled into the process.

The molar ratio of the nitrile component II to the alcohol is to range from 1:1 to 1:10, preferably 1:1.1 to 1:2.5.

The temperature in the reactor is between 30° C. and a maximum of about 5° C. below the boiling point of the alcohol that is used, but it is preferably in the range from 50° to 100° C., and in the case of low-boiling alcohols in the range from 50° to 62° C. The temperature of the starting materials is not critical, but to reduce the average time of stay it is to be preferably close to the subsequent reaction temperature.

The catalyst concentration is to range from 0.05 to 15%, preferably 0.5 to 2.5%, with respect to the weight of the alcohol.

The nitrile component can be used undiluted or diluted with the alcohol.

Surprisingly, the average time of stay in the continuous-flow reactor ranges from 2 to 120 minutes, preferably from 5 to 60 minutes.

It is important that the distillation of the reaction mixture, separation of the alcohol and final distillation of the product be performed in a vacuum if otherwise there is danger of decomposition of the product, regardless of whether the distillation is a continuous or batch process.

The alcohol that is separated in high purity is recycled to the process.

The cyanacetaldehyde acetals are valuable starting substances for the synthesis of numerous pharmaceutical compounds, such as, for example, 5-aryl substituted 2,4-diaminopyrimidines (trimethoprin) (DE-OS No. 3 014 412)

EXAMPLES

Example 1

In a continuous-flow reactor consisting of a heated 250 ml four-necked flask with a dual introduction tube, stirrer, internal thermometer, and a superimposed, thermostatically controlled intensive condenser as heat exchanger, 3-ethoxypropenenitrile and 1.5 wt.-% ethanolic solution of sodium ethoxide are fed continuously at room temperature with thorough stirring. After the reaction begins, the internal temperature of the reactor is held at 60° C. by heating or cooling as required. 417.4 g, corresponding to 441.7 ml, of 3-ethoxy-propenenitrile and 341.0 g, corresponding to 432 ml, of alcoholate solution is metered per hour into the reactor. The average time of stay as defined above is 55 minutes.

The reaction mixture emerging from the top of the reactor is continuously cooled down to room temperature by means of a descending product condenser, and a regular, slow stream of dry carbon dioxide is introduced into this cooled solution with intensive stirring.

The gas chromatographic analysis of the reaction suspension shows a transformation of more than 99.2% of the input 3-ethoxypropenenitrile. 343.4 g of this reaction suspension is distilled under a slow stream of carbon dioxide at standard pressure and then at 15 mbar in a 30-centimeter Vigreux column. 63.5 g of ethanol is obtained, which is recycled into the process, 20.3 g as first-runnings of the vacuum distillation and 251.2 g of 3,3-diethoxypropanenitrile. 5.8 g remain as distillation residue. The first-runnings contain, according to gas chromatographic analysis, 95.0 Flä-% of target product, and are recycled to the reactor.

The main product fraction has a purity of more than 99%. The total yield of product amounts to 96.1% of the theory.

Example 2

Similarly to Example 1, preheated reaction component is now metered into the reactor, namely, 669.4 g of 1.5 weight-percent ethanolic sodium ethoxide solution of 46° C. and 639.8 g of 3-ethoxypropenenitrile preheated to 50° C., per hour. Mean time of stay: 31.5 minutes.

The catalyst deactivation and the working up of the reaction suspension are performed as in Example 1. The transformation, as determined by gas chromatography, is more than 99.5% with respect to the compound of formula II. The yield is 96.8% of the theory (I with respect to II). Purity of the principal faction: more than 99.0%.

It will be understood that the specification and examples are illustrative but not limitative of the present invention and that other embodiments within the spirit and scope of the invention will suggest themselves to those skilled in the art.

Example 3

Using the same continuous-flow reactor as described in Example 1 and similarly to Example 2, preheated components are also used for the synthesis of 3,3-dimethoxy-propanenitrile:

598,6 g of 1,5 weight-percent methanolic sodium methoxide, preheated to 50° C., and 776,4 g of 3-methoxy-propanenitrile, preheated to 45° C., are now metered in the reactor per hour. The internal reaction temperature in the reactor is held at 55° C. The time of stay as defined before is 30 minutes.

The catalyst deactivating and the working up of the reaction suspension are performed as in Example 1. The transformation, as determined by gas chromatography, is more than 99% with respect to 3-methoxypropenenitrile (component of formula II).

Distilling a 450 g sample of this suspension, there were obtained 93,5 g of methanol, 15,5 g as first-runnings of the vacuum-distillation and 335 g of 3,3-dimethoxy-propanenitrile (boiling temperature at 15 millibars 79°–84° C.) as the target product; 5,0 g remain as distillation residue. The main product fraction has a purity of more than 98,5%; the total yield of product amounts to 96% of the theory.

What is claimed is:

1. A method of preparing cyanacetaldehyde acetals of the formula

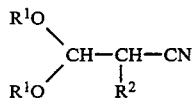
  I wherein $R^1$ represents identical or different straight-chain or branched alkyl moieties of 1 to 20 carbon atoms, or —$(CH_2)_m$—Cyc, Cyc being carbon isocyclic or mononuclear or polynuclear, carbocyclic aromatic with m=0 to 5, or one of the moieties $R^1$ or both of the moieties $R^1$ representing —(alkylene)$_p$—OH with p=2 to 6, and wherein $R^2$ represents H, $R^1$, or the moieties —$(CH_2)_m$—$OR^3$ or —$(CH_2)_m$—$CH(OR^3)_2$, $R^3$ representing straight-chain or branched chain alkyl moieties of 1 to 12 carbon atoms and m and Cyc having the meanings given above, comprising the steps of:

reacting at temperatures in the range of 50° to 100° C., compounds of the formula

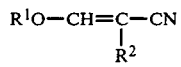
  II wherein $R^1$ and $R^2$ have the above meaning, with alcohols of the formula $R^1$—OH   III wherein $R^1$ has the same meaning, in a molar ratio of compounds of formula II to alcohols of formula III in the ranges of 1:1 to 1:10, in the presence of a basic catalyst of the formula $M(OR^1)_n$   IV wherein M is an alkali metal with n=1 or an alkaline earth metal with n=2 and $R^1$ has the same meaning as above, and which is dissolved or suspended in the alcohol component, said catalyst concentration being maintained in the range of 0.5 to 2.5 wt.% with respect to the alcohol; and thereafter deactivating the catalyst with carbon dioxide or an inorganic or organic acid with the exception of sulfuric and/or acetic acid.

2. The method of claim 1 wherein the process is performed continuously in a continuous-flow reactor with an average time of stay therein predetermined by the fill capacity of the reactor and the total volume of starting substances at 20° C. which is fed into the reactor per hour.

3. The method of claim 2, wherein the average time of stay ranges from 2 to 120 minutes.

4. The method of claim 3 wherein the time of stay ranges from 5 to 60 minutes.

5. The method of claim 1 wherein the nitrile component and the alcohol component are fed into the reactor separately and continuously.

6. The method of claim 5, further comprising preheating the nitrile component and the alcohol component to at least about 20° C. before feeding into the reactor.

7. The method of claim 2 wherein the reaction temperature is in the range 30° C. to approximately 5° C. below the boiling temperature of the alcohol used.

8. The method of claim 1 wherein the molar range is 1:1.1 to 1:2.5.

9. The method of claim 1 wherein the basic catalyst is metered into the reactor continuously and in dissolved form.

10. The method of claim 9, wherein the catalyst is dissolved in the alcohol component.

11. The method of claim 1 wherein the catalyst concentration is maintained in the range of 0.05 to 15 wt.-% with respect to the amount of the alcohol.

12. The method of claim 1 wherein catalyst deactivation is accomplished with dry carbon dioxide by introduction and dispersion in vacuo, at standard pressure or at excess pressure.

13. The method of claim 1 wherein catalyst deactivation is performed continuously.

14. The method of claim 1 wherein catalyst deactivation is performed in a batch process.

15. The method of claim 1 wherein the reaction suspensions are worked-up by distillation under reduced pressure in a carbon dioxide atmosphere.

16. The continuous method of claim 2 wherein the product is worked up by fractional distillation and the preliminary fraction produced in the fractional distillation of the product and containing unreacted starting material and product is returned to continuous flow reaction circuit.

17. The method of claim 1, wherein $R^1$ is an alkyl moiety of 1 to 3 carbon atoms and wherein $R^2$ is H, $R^1$, phenyl, benzyl, cyclopentyl, cyclohexyl and cycloheptyl.

* * * * *